(12) United States Patent
Liao et al.

(10) Patent No.: US 12,116,340 B2
(45) Date of Patent: *Oct. 15, 2024

(54) METHOD FOR MANUFACTURING METHYLTETRAHYDROPHTHALIC ANHYDRIDE

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Jung-Tsu Wu, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,943

(22) Filed: Dec. 21, 2022

(65) Prior Publication Data
US 2024/0140900 A1      May 2, 2024

(30) Foreign Application Priority Data

Oct. 28, 2022   (TW) .................. 111141030

(51) Int. Cl.
*C07C 51/56*    (2006.01)
*C07D 307/89*   (2006.01)

(52) U.S. Cl.
CPC ............ *C07C 51/56* (2013.01); *C07D 307/89* (2013.01)

(58) Field of Classification Search
CPC ........................................ C07C 51/56
See application file for complete search history.

(56) References Cited

U.S. PATENT DOCUMENTS 3,976,590 A    8/1976   Yax et al.

FOREIGN PATENT DOCUMENTS

| CN | 109824639 A | 5/2019 | |
|----|-------------|--------|---|
| CN | 211005192 U | 7/2020 | |
| CN | 114669256 A | 6/2022 | |
| DE | 102010029587 A1 | 12/2010 | |
| JP | 57206678 A | 12/1982 | |
| JP | 2002155070 A | 5/2002 | |
| JP | 4774591 | * 9/2011 | ........... C07D 307/89 |

* cited by examiner

*Primary Examiner* — Nizal S Chandrakumar
(74) *Attorney, Agent, or Firm* — Li & Cai Intellectual Property Office

(57) ABSTRACT

A method for manufacturing methyltetrahydrophthalic anhydride is provided, which includes steps as follows. Maleic anhydride is added into a reactor. Piperylene is added into the reactor, so that the piperylene and the maleic anhydride undergo a first addition reaction. When a conversion rate of the maleic anhydride is more than 25%, the first addition reaction is completed. Isoprene is added into the reactor, so that the isoprene and the maleic anhydride undergo a second addition reaction to obtain a methyltetrahydrophthalic anhydride product. The methyltetrahydrophthalic anhydride product contains 3-methyltetrahydrophthalic anhydride and 4-methyltetrahydrophthalic anhydride.

10 Claims, 2 Drawing Sheets

METHOD FOR MANUFACTURING METHYLTETRAHYDROPHTHALIC ANHYDRIDE

CROSS-REFERENCE TO RELATED PATENT APPLICATION

This application claims the benefit of priority to Taiwan Patent Application No. 111141030, filed on Oct. 28, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for manufacturing methyltetrahydrophthalic anhydride, and more particularly to a method for manufacturing methyltetrahydrophthalic anhydride with high reaction efficiency.

BACKGROUND OF THE DISCLOSURE

Methyltetrahydrophthalic anhydride is a hardener commonly used in organic acid anhydride epoxy resins. The methyltetrahydrophthalic anhydride has good heat resistance and stability, while still maintaining good physical and electrical properties even under high temperature environments.

Generally speaking, reactants for synthesizing the methyltetrahydrophthalic anhydride include piperylene, isoprene and acid anhydride. A conventional method for manufacturing the methyltetrahydrophthalic anhydride is to add the metered reactants into a reactor all at a time, so that the reactants undergo the Diels-Alder reaction (also known as a conjugated diene addition reaction). Accordingly, the methyltetrahydrophthalic anhydride can be generated.

Through a careful observation of reaction steps, it can be found that the acid anhydride is a limiting reagent in the reaction, and the piperylene and the isoprene are excess reactants. In the early stage of the reaction, there is a competitive reaction between the piperylene and the isoprene. In the middle and later stages of the reaction, the concentration of the acid anhydride is low, which is not conducive to a reaction progress. In order to achieve a higher conversion rate, the conventional method for manufacturing the methyltetrahydrophthalic anhydride usually has a longer reaction time or a higher reaction temperature, and thus has problems that include high manufacturing costs and high energy consumption.

Therefore, how to enhance a reaction efficiency of the reactants through an improvement of the steps, so as to overcome the above-mentioned deficiencies, has become one of the important issues to be addressed in the industry.

SUMMARY OF THE DISCLOSURE

In response to the above-referenced technical inadequacies, the present disclosure provides a method for manufacturing methyltetrahydrophthalic anhydride.

In one aspect, the present disclosure provides a method for manufacturing methyltetrahydrophthalic anhydride. The method includes steps as follows. Maleic anhydride is added into a reactor. Piperylene is added into the reactor, so that the piperylene and the maleic anhydride undergo a first addition reaction. When a conversion rate of the maleic anhydride is more than 25%, the first addition reaction is completed. Isoprene is added into the reactor, so that the isoprene and the maleic anhydride undergo a second addition reaction to obtain a methyltetrahydrophthalic anhydride product. The methyltetrahydrophthalic anhydride product contains 3-methyltetrahydrophthalic anhydride and 4-methyltetrahydrophthalic anhydride.

In certain embodiments, the first addition reaction is performed at a temperature of 80° C. to 120° C., and the second addition reaction is performed at a temperature of 80° C. to 120° C.

In certain embodiments, a weight ratio of the 3-methyltetrahydrophthalic anhydride to the 4-methyltetrahydrophthalic anhydride is 7:3 to 3:7.

In certain embodiments, a content ratio of trans-3-methyltetrahydrophthalic anhydride to cis-3-methyltetrahydrophthalic anhydride in the methyltetrahydrophthalic anhydride product is 1:4 to 1:7.

In certain embodiments, when a content of the maleic anhydride is less than 100 ppm, the second addition reaction is completed.

In certain embodiments, the method further includes: performing an isomerization reaction between the methyltetrahydrophthalic anhydride product and an alkaline catalyst to obtain an isomerization product. The isomerization product contains 3-methyltetrahydrophthalic anhydride and 4-methyltetrahydrophthalic anhydride tetrahydrophthalic anhydride.

In certain embodiments, the alkaline catalyst is selected from the group consisting of potassium carbonate, sodium carbonate, sodium hydroxide, potassium hydroxide, ethanolamine, diethanolamine and triethanolamine.

In certain embodiments, the isomerization reaction is performed at a temperature of 130° C. to 160° C.

In certain embodiments, a content ratio of trans-3-methyltetrahydrophthalic anhydride to cis-3-methyltetrahydrophthalic anhydride in the isomerization product is 1.1:1 to 4.8:1.

In certain embodiments, a viscosity of the isomerization product is 30 cps to 50 cps.

In certain embodiments, a purity of the piperylene is 65% to 75%, and a purity of the isoprene is more than 99%.

Therefore, in the method for manufacturing the methyltetrahydrophthalic anhydride provided by the present disclosure, by virtue of "adding piperylene into the reactor, so that the piperylene and the maleic anhydride undergo a first addition reaction" and "adding isoprene into the reactor, so that the isoprene and the maleic anhydride undergo a second addition reaction," reactants can have an improved reaction efficiency. In this way, the reaction can be performed at a low temperature.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
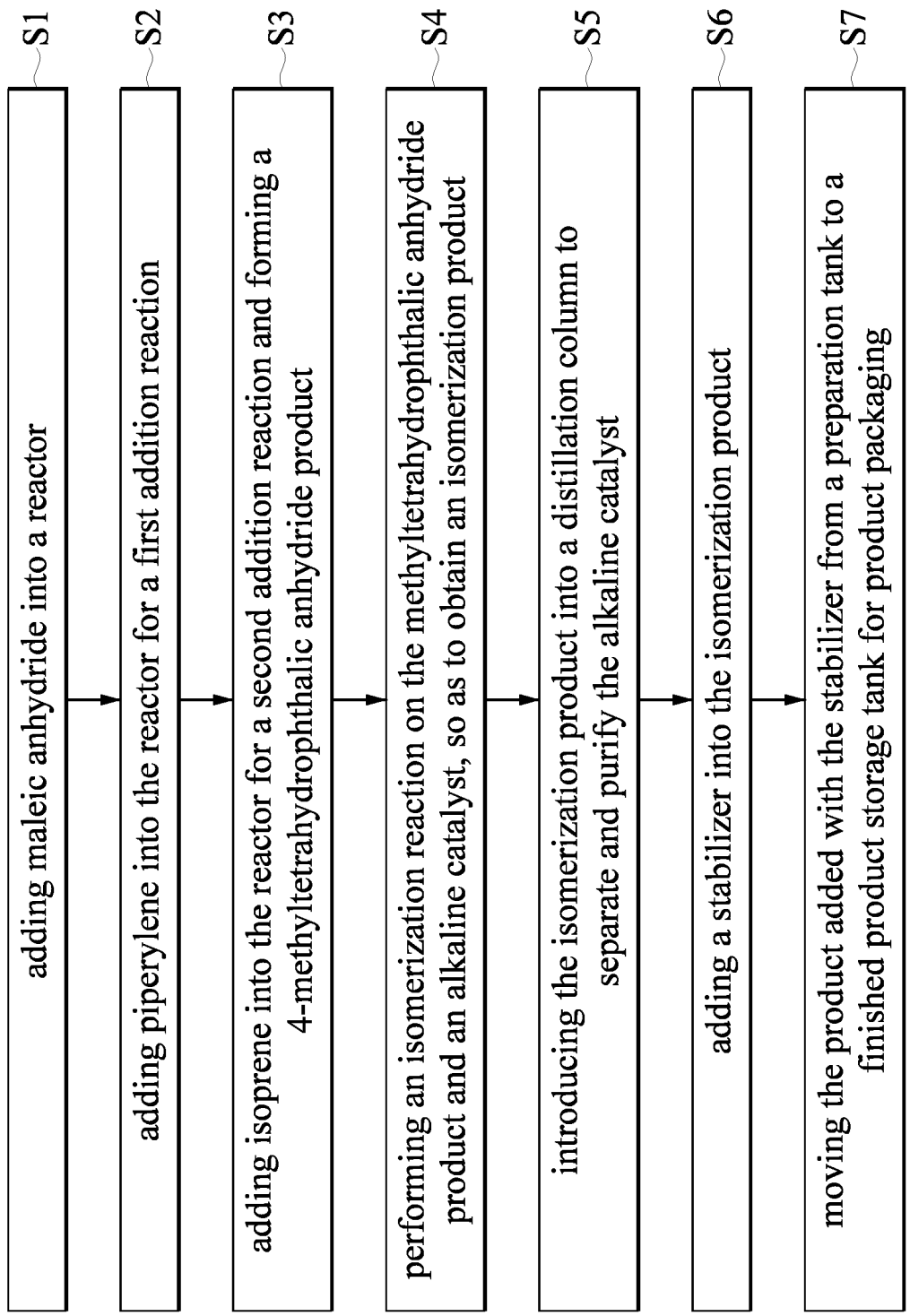
FIG. 1 is a flowchart of a method for manufacturing methyltetrahydrophthalic anhydride according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Different from adding reactants all at a time (i.e., piperylene and isoprene simultaneously undergoing an addition reaction), the reactants are added in stages (i.e., piperylene and isoprene being added in a stepwise manner) for undergoing two addition reactions in the present disclosure. In this way, reaction efficiency for manufacturing methyltetrahydrophthalic anhydride can be improved.

In the first addition reaction, maleic anhydride is an excess reagent, piperylene is a limiting reagent, and 3-methyltetrahydrophthalic anhydride can be generated by a reaction between the maleic anhydride and the piperylene. In the second addition reaction, maleic anhydride is a limiting reagent, isoprene is an excess reagent, and 4-methyltetrahydrophthalic anhydride can be generated by a reaction between the remaining maleic anhydride and the isoprene. After the two addition reactions (the first addition reaction and the second addition reaction), a methyltetrahydrophthalic anhydride product contains 3-methyltetrahydrophthalic anhydride and 4-methyltetrahydrophthalic anhydride. In this way, the competitive reaction between piperylene and isoprene can be avoided, so as to achieve the effect of improving the reaction efficiency of the reactants.

Through the technical solution of adding the reactants in stages, a content ratio of 3-methyltetrahydrophthalic anhydride and 4-methyltetrahydrophthalic anhydride in the methyltetrahydrophthalic anhydride product can be easily controlled. Further, methyltetrahydrophthalic anhydride products with expected properties can be produced according to practical requirements.

Figure 2:
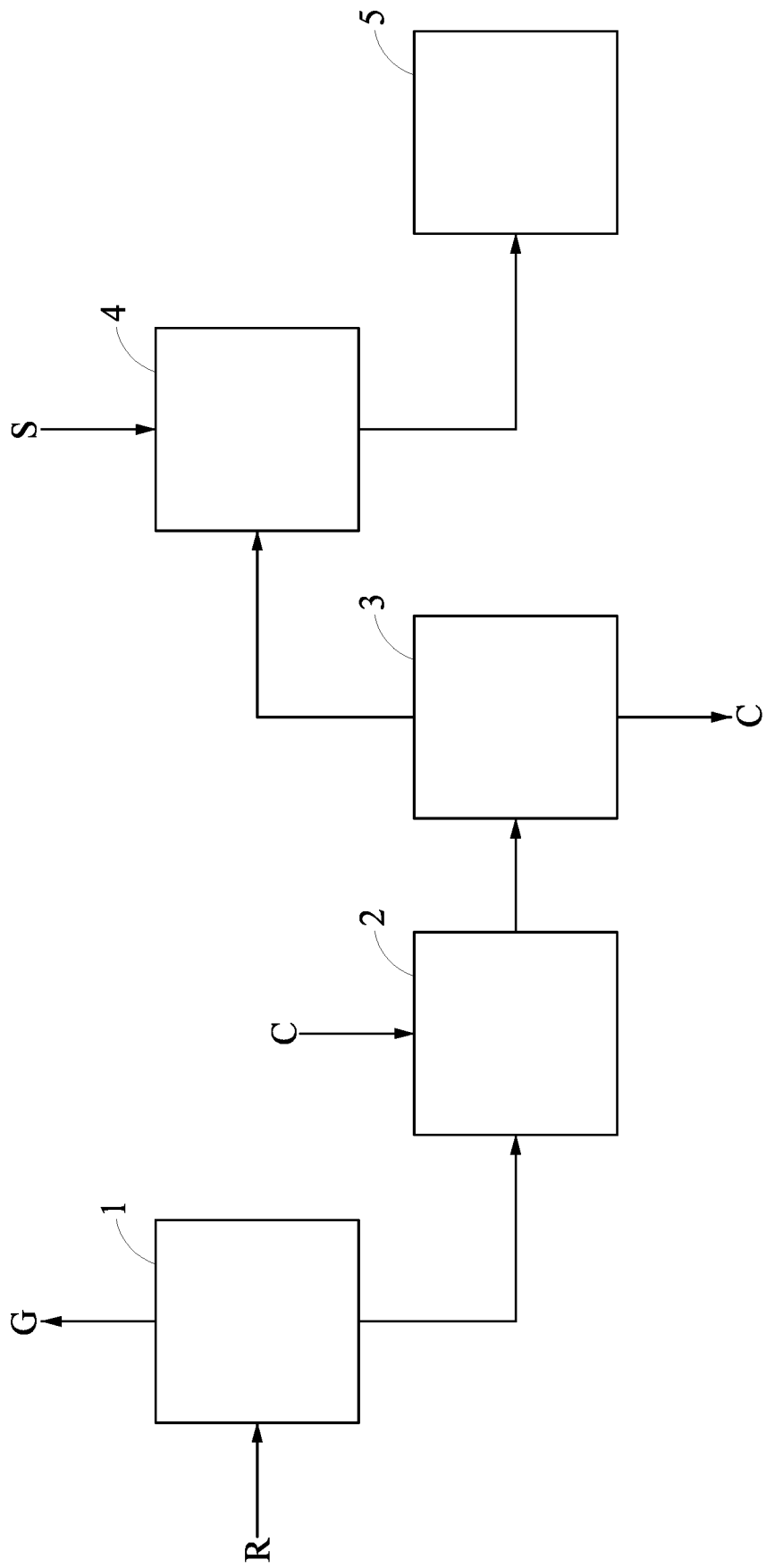
FIG. 2 is a schematic view illustrating an apparatus for manufacturing the methyltetrahydrophthalic anhydride according to the present disclosure.

Reference is made to FIG. 1 and FIG. 2. FIG. 1 is a flowchart of a method for manufacturing methyltetrahydrophthalic anhydride according to the present disclosure, and FIG. 2 is a schematic view illustrating an apparatus for manufacturing the methyltetrahydrophthalic anhydride according to the present disclosure. The apparatus shown in FIG. 2 can be used to implement the method of the present disclosure, but the steps in the present disclosure will not be limited thereby.

In steps S1 to S3, a reactant R (maleic anhydride, piperylene and isoprene) is added into a reactor 1. After two addition reactions (a first addition reaction and a second addition reaction), a methyltetrahydrophthalic anhydride product of a crystalline solid state can be formed. Since an impurity G in the reactant R (especially the impurity in the piperylene) does not react with the maleic anhydride, after the methyltetrahydrophthalic anhydride product is generated, the impurity G can be discharged from the reactor 1 in the form of a gas and separated from the methyltetrahydrophthalic anhydride product.

In step S1, maleic anhydride is added into the reactor 1. By heating the reactor 1 to a temperature of from 60° C. to 75° C., maleic anhydride is in a liquid state (which facilitates the reaction).

In step S2, piperylene is added into the reactor 1. Specifically, the piperylene is introduced into the reactor 1 in the form of a gas. The reactor 1 is heated to a temperature of 80° C. to 120° C., so as to perform the first addition reaction. In the first addition reaction, maleic anhydride reacts with piperylene to form 3-methyltetrahydrophthalic anhydride.

Due to the difference in the three-dimensional structure, the 3-methyltetrahydrophthalic anhydride generated in the first addition reaction has an optical isomer. Specifically, a content of trans-3-methyltetrahydrophthalic anhydride is less than a content of cis-3-methyltetrahydrophthalic anhydride. In one exemplary embodiment, a content ratio of trans-3-methyltetrahydrophthalic anhydride to cis-3-methyltetrahydrophthalic anhydride is 1:4 to 1:7 (e.g., 1:4.5, 1:5, 1:5.5, 1:6, or 1:6.5). If a ratio between trans-3-methyltetrahydrophthalic anhydride and cis-3-methyltetrahydrophthalic anhydride is to be further adjusted, the tetrahydrophthalic anhydride product can be subjected to an isomerization reaction (step S4). Regarding the isomerization reaction, specific steps thereof will be described in following paragraphs.

By adjusting the time taken for the first addition reaction, the effect of controlling the content ratio of 3-methyltetrahydrophthalic anhydride and 4-methyltetrahydrophthalic anhydride in the methyltetrahydrophthalic anhydride product can be achieved. In the present disclosure, when a conversion rate of maleic anhydride is more than 25%, the first addition reaction is completed. That is, in the to-be-generated methyltetrahydrophthalic anhydride of the present disclosure, the content of 3-methyltetrahydrophthalic anhydride is at least 25 wt %. Specifically, the first addition reaction can optionally be stopped when the conversion rate of maleic anhydride reaches 30%, 35%, 40%, 45%, 50%, 55%, 60%, 65%, 70%, 75% or 80%.

Since a melting point of 3-methyltetrahydrophthalic anhydride is lower than that of 4-methyltetrahydrophthalic anhydride, when the content of 3-methyltetrahydrophthalic anhydride in the methyltetrahydrophthalic anhydride product is higher, the methyltetrahydrophthalic anhydride product may have a lower viscosity. When the content of 3-methyltetrahydrophthalic anhydride in the methyltetrahydrophthalic anhydride product is lower, the methyltetrahydrophthalic anhydride product may have a higher viscosity. Simply speaking, in the present disclosure, a component ratio or characteristics (e.g. viscosity) of the methyltetrahydrophthalic anhydride product can be controlled by adjusting the time by which the first addition reaction ends.

In step S3, isoprene is added into the reactor 1. Specifically, the isoprene is introduced into the reactor 1 in the form of a gas. The reactor 1 is heated to a temperature of 80° C. to 120° C., so as to perform the second addition reaction. In the second addition reaction, maleic anhydride reacts with isoprene to form 4-methyltetrahydrophthalic anhydride. In order to reduce production costs, when a content of maleic anhydride is less than 100 ppm, the second addition reaction is completed. However, the present disclosure is not limited thereto.

Through the above-mentioned first addition reaction and second addition reaction (steps S1 to S3), the methyltetrahydrophthalic anhydride product of a crystalline solid state can be obtained. The methyltetrahydrophthalic anhydride product contains 3-methyltetrahydrophthalic anhydride and 4-methyltetrahydrophthalic anhydride. In addition, the content ratio of 3-methyltetrahydrophthalic anhydride and 4-methyltetrahydrophthalic anhydride can be adjusted by the reaction time of the first addition reaction. In one exemplary embodiment, the content ratio of 3-methyltetrahydrophthalic anhydride to 4-methyltetrahydrophthalic anhydride is 7:3 to 3:7. For example, the content ratio of 3-methyltetrahydrophthalic anhydride to 4-methyltetrahydrophthalic anhydride may be 6:4, 5:5 or 4:6.

In addition, the purity of the reactants also affects the reaction rate of the reaction. The purity of piperylene currently available on the market is generally lower than that of isoprene. Therefore, piperylene is added before isoprene in the present disclosure. In the first addition reaction, maleic anhydride has not yet reacted and thus has a high concentration, which can be used to overcome a problem of low reaction rate caused by the piperylene having a low purity. In the second addition reaction, maleic anhydride has reacted with piperylene to form 3-methyltetrahydrophthalic anhydride, so that the concentration of maleic anhydride is low. Therefore, isoprene with a high purity can be used to overcome the problem of low reaction rate caused by the maleic anhydride having a lower concentration. Accordingly, the method for manufacturing the methyltetrahydrophthalic anhydride of the present disclosure can achieve the effect of improving the reaction efficiency.

In the embodiments of the present disclosure, the purity of piperylene is below 80% (65% to 75%), and the purity of isoprene is above 99%. However, the present disclosure is not limited thereto.

After the methyltetrahydrophthalic anhydride product is obtained, according to practical requirements, the characteristics of the methyltetrahydrophthalic anhydride product can be further adjusted through steps S4 to S6.

In step S4, the methyltetrahydrophthalic anhydride product is transported to an isomerization tank 2, so that an isomerization reaction is performed between the methyltetrahydrophthalic anhydride product and an alkaline catalyst C at a temperature of 13° C. to 160° C. for obtaining an isomerization product. Specifically, step S4 is to perform the isomerization reaction on 3-methyltetrahydrophthalic anhydride in the methyltetrahydrophthalic anhydride product. In this way, cis-3-methyltetrahydrophthalic anhydride can be reconstituted into trans-3-methyltetrahydrophthalic anhydride, so as to adjust the content ratio of trans-3-methyltetrahydrophthalic anhydride to cis-3-methyltetrahydrophthalic anhydride.

Before the isomerization reaction, the content of trans-3-methyltetrahydrophthalic anhydride is lower than the content of cis-3-methyltetrahydrophthalic anhydride in the methyltetrahydrophthalic anhydride product. After the isomerization reaction, the content of trans-3-methyltetrahydrophthalic anhydride is higher than that of cis-3-methyltetrahydrophthalic anhydride in the isomerization product. The content ratio of trans-3-methyltetrahydrophthalic anhydride to cis-3-methyltetrahydrophthalic anhydride in the isomerization product can be tracked by a gas chromatograph (brand: Agilent, model: 8860 GC). In one exemplary embodiment, the content ratio of trans-3-methyltetrahydrophthalic anhydride to cis-3-methyltetrahydrophthalic anhydride is 1.1:1 to 4.8:1 (e.g., 1.5:1, 2:1, 2.5:1, 1, 3:1, 3.5:1, 4:1 or 4.5:1).

When the content of trans-3-methyltetrahydrophthalic anhydride in the isomerization product is increased, the viscosity of the isomerization product can be reduced, so that the final product can have a wider applicability. Specifically, the viscosity of the isomerization product may range from 30 cps to 50 cps (e.g., 35 cps, 40 cps or 45 cps).

The alkaline catalyst C used in the isomerization reaction can be an organic base or an inorganic base, and the organic base can be an alcohol amine (especially one selected from the group consisting of: ethanolamine, diethanolamine and triethanolamine) The inorganic base may be selected from the group consisting of potassium carbonate, sodium carbonate, sodium hydroxide and potassium hydroxide.

In step S5, the isomerization product is introduced into a distillation column 3 to separate and purify the alkaline catalyst C. In step S6, the isomerization product is moved from the distillation column 3 to a preparation tank 4, and a stabilizer S (e.g., butylated hydroxytoluene (BHT)) can be optionally added to increase the product shelf life. However, the present disclosure is not limited thereto. In step S7, the product added with the stabilizer S is moved from the preparation tank 4 to a finished product storage tank 5 for product packaging.

With regard to the method for manufacturing the methyltetrahydrophthalic anhydride of the present disclosure, the following Examples 1 to 7 are exemplarily provided for convenience of description. Reaction parameters in Examples 1 to 3 are shown in Table 1, and reaction parameters in Examples 4 to 7 are shown in Table 2.

Example 1

6,000 kilograms of the maleic anhydride are added into the reactor, and the reactor is heated to melt the maleic anhydride. When the temperature of the reactor reaches 70° C., the piperylene after vaporization is introduced into the reactor for the first addition reaction. During the first addition reaction, the conversion rate of the maleic anhydride is tracked by a gas chromatograph. When the conversion rate of the maleic anhydride reaches 70% (which takes 12 hours), the introduction of the piperylene is stopped for completion of the first addition reaction.

The isoprene after vaporization is introduced into the reactor for the second addition reaction. During the second addition reaction, the content of the maleic anhydride is tracked by the gas chromatograph. When the content of the maleic anhydride is lower than 100 ppm (which takes 4 hours), the introduction of the isoprene is stopped for completion of the second addition reaction. After the residual gas in the reactor is discharged, the methyltetrahydrophthalic anhydride product can be obtained.

In Example 1, a weight ratio of 3-methyltetrahydrophthalic anhydride to 4-methyltetrahydrophthalic anhydride in the methyltetrahydrophthalic anhydride product is 7:3, and the content ratio of trans-3-methyltetrahydrophthalic anhydride to cis-3-methyltetrahydrophthalic anhydride in 3-methyltetrahydrophthalic anhydride is 1:5.6.

Then, the methyltetrahydrophthalic anhydride product is transported to the isomerization tank, and sodium hydroxide (alkaline catalyst) is added into the isomerization tank. The isomerization reaction is performed at a temperature of 150° C. for 24 hours, so as to obtain the isomerization product. According to detection made by the gas chromatograph, the content ratio of trans-3-methyltetrahydrophthalic anhydride to cis-3-methyltetrahydrophthalic anhydride in the isomerization product is 4.31:1, and the viscosity of the isomerization product is 33 cps. Afterwards, a final isomerization product can be obtained through the above-mentioned steps S5 to S7.

Example 2

6000 kilograms of maleic anhydride are added into the reactor, and the reactor is heated up to melt the maleic anhydride. When the temperature of the reactor reaches 100° C., the piperylene after vaporization is introduced into the reactor for the first addition reaction. During the first addition reaction, the conversion rate of maleic anhydride is tracked with the gas chromatograph. When the conversion rate of maleic anhydride reaches 50% (takes 8.5 hours), the introduction of piperylene is stopped to complete the first addition reaction.

The isoprene after vaporization is introduced into the reactor for the second addition reaction. During the second addition reaction, the content of maleic anhydride is tracked with a gas chromatograph. When the content of maleic anhydride is lower than 100 ppm (takes 6 hours), the introduction of isoprene is stopped to complete the second addition reaction. After the residual gas in the reactor is discharged, the methyltetrahydrophthalic anhydride product can be obtained.

In the second embodiment, the weight ratio of 3-methyltetrahydrophthalic anhydride and 4-methyltetrahydrophthalic anhydride in the methyltetrahydrophthalic anhydride product is 1:1, and the content ratio of trans-3-methyltetrahydrophthalic anhydride to cis-3-methyltetrahydrophthalic anhydride in 3-methyltetrahydrophthalic anhydride is 1:5.2.

Afterwards that, the methyltetrahydrophthalic anhydride product is transported to the isomerization tank, and sodium hydroxide (alkaline catalyst) is added into the isomerization tank for the isomerization reaction performed at a temperature of 150° C. for 20 hours to obtain the isomerization product. After detection by gas chromatography, the content ratio of trans-3-methyltetrahydrophthalic anhydride to cis-3-methyltetrahydrophthalic anhydride in the isomerization product is 3.5:1, and the viscosity of the isomerization product is 36 cps. After that, a final isomerization product can be obtained through the above S5 to S7.

Example 3

6000 kilograms of maleic anhydride are added in the reactor, and the reactor is heated up to melt the maleic anhydride. When the temperature of the reactor reaches 100° C., the piperylene after vaporization is introduced into the reactor for the first addition reaction. During the first addition reaction, the conversion rate of maleic anhydride is tracked with the gas chromatograph. When the conversion rate of maleic anhydride reaches 30% (takes 4 hours), the introduction of piperylene is stopped to complete the first addition reaction.

The isoprene after vaporization is introduced into the reactor for the second addition reaction. During the second addition reaction, the content of maleic anhydride is tracked with a gas chromatograph. When the content of maleic anhydride is lower than 100 ppm (takes 8 hours), the introduction of isoprene is stopped to complete the second addition reaction. After the residual gas in the reactor is discharged, the methyltetrahydrophthalic anhydride product can be obtained.

In the third embodiment, the weight ratio of 3-methyltetrahydrophthalic anhydride and 4-methyltetrahydrophthalic anhydride in the methyltetrahydrophthalic anhydride product is 3:7, and the content ratio of trans-3-methyltetrahydrophthalic anhydride to cis-3-methyltetrahydrophthalic anhydride in 3-methyltetrahydrophthalic anhydride is 1:5.5.

The methyltetrahydrophthalic anhydride product is transported to the isomerization tank, and sodium hydroxide (alkaline catalyst) is added into the isomerization tank for the isomerization reaction performed at a temperature of 150° C. for 16 hours to obtain the isomerization product. After detection by gas chromatography, the content ratio of trans-3-methyltetrahydrophthalic anhydride and cis-3-methyltetrahydrophthalic anhydride in the isomerization product is 4.1:1, and the viscosity of the isomerization product is 40 cps. After that, a final isomerization product can be obtained through the above S5 to S7.

TABLE 1

| | Example 1 | Example 2 | Example 3 |
|---|---|---|---|
| Conversion rate of maleic anhydride at the end of the first addition reaction | 70% | 50% | 30% |
| First addition reaction time | 12 hours | 8.5 hours | 4 hours |
| Second addition reaction time | 4 hours | 6 hours | 8 hours |
| Weight ratio of 3-methyltetrahydrophthalic anhydride to 4-methyltetrahydrophthalic anhydride in the methyltetrahydrophthalic anhydride product | 7:3 | 1:1 | 3:7 |
| Content ratio of trans-3-methyltetrahydrophthalic anhydride to cis-3-methyltetrahydrophthalic anhydride in methyltetrahydrophthalic anhydride product | 1:5.6 | 1:5.2 | 1:5.5 |

TABLE 1-continued

|  | Example 1 | Example 2 | Example 3 |
|---|---|---|---|
| Alkaline catalyst | Sodium hydroxide | Sodium hydroxide | Sodium hydroxide |
| Isomerization reaction temperature | 150° C. | 150° C. | 150° C. |
| Isomerization reaction time | 24 hours | 20 hours | 16 hours |
| Content ratio of trans-3-methyltetrahydrophthalic anhydride to cis-3-methyltetrahydrophthalic anhydride in the isomerization product | 4.31:1 | 3.5:1 | 4.1:1 |
| Isomerization product viscosity | 33 cps | 36 cps | 40 cps |

It can be observed from the content of Examples 1 to 3 that the content ratio of 3-methyltetrahydrophthalic anhydride to 4-methyltetrahydrophthalic anhydride in the methyltetrahydrophthalic anhydride product can be easily adjusted through the technical solution of adding the reactants in stages as proposed in the present disclosure. The reaction efficiency of the reactants can also be improved through the technical solution of adding the reactants in stages, so that the two addition reactions can be performed at a lower temperature. Furthermore, by adjusting the content ratio of 3-methyltetrahydrophthalic anhydride to 4-methyltetrahydrophthalic anhydride in the methyltetrahydrophthalic anhydride product, and adjusting the content ratio of trans-3-methyltetrahydrophthalic anhydride to cis-3-methyltetrahydrophthalic anhydride in the isomerization product, the effect of controlling the viscosity of the product can be achieved. Specifically, the viscosity of the isomerization product is 32 cps to 42 cps.

Example 4

A hardener crude product having a total weight of 10,000 kilograms is added into an isomerization tank, and the hardener crude product includes 7,000 kilograms of 3-methyltetrahydrophthalic anhydride (the content ratio of trans-3-methyltetrahydrophthalic anhydride to cis-3-methyltetrahydrophthalic anhydride being 1:5.6) and 3,000 kilograms of 4-methyltetrahydrophthalic anhydride.

After adding 60 kilograms of sodium hydroxide (alkaline catalyst), the isomerization reaction is performed at a temperature of 140° C. for 24 hours to obtain an isomerization product. According to detection made by the gas chromatograph, the content ratio of trans-3-methyltetrahydrophthalic anhydride to cis-3-methyltetrahydrophthalic anhydride in the isomerization product is 4.03:1, and the viscosity of the isomerization product is 34 cps. Afterwards, a final isomerization product can be obtained through the above-mentioned steps S5 to S7.

Example 5

10,000 kilograms of gross weight of hardener crude product are added into an isomerization tank, and the hardener crude product includes 7,000 kilograms of 3-methyltetrahydrophthalic anhydride (the content ratio of trans-3-methyltetrahydrophthalic anhydride to cis-3-methyltetrahydrophthalic anhydride is 1:5.6) and 3,000 kilograms of 4-methyltetrahydrophthalic anhydride.

After adding 60 kilograms of diethanolamine (alkaline catalyst), the isomerization reaction is performed at a temperature of 140° C. for 24 hours to obtain an isomerization product. After detection by gas chromatography, the content ratio of trans-3-methyltetrahydrophthalic anhydride and cis-3-methyltetrahydrophthalic anhydride in the isomerization product is 1.19:1, and the viscosity of the isomerization product is 37 cps. After that, a final isomerization product can be obtained through the above S5 to S7.

Example 6

A hardener crude product having a total weight of 10,000 kilograms is added into an isomerization tank, and the hardener crude product includes 7,000 kilograms of 3-methyltetrahydrophthalic anhydride (the content ratio of trans-3-methyltetrahydrophthalic anhydride to cis-3-methyltetrahydrophthalic anhydride is 1:5.6) and 3,000 kilograms of 4-methyltetrahydrophthalic anhydride.

After adding 60 kilograms of sodium hydroxide (alkaline catalyst), the isomerization reaction is performed at a temperature of 150° C. for 24 hours to obtain an isomerization product. After detection by gas chromatography, the content ratio of trans-3-methyltetrahydrophthalic anhydride and cis-3-methyltetrahydrophthalic anhydride in the isomerization product is 4.31:1, and the viscosity of the isomerization product is 33 cps. After that, a final isomerization product can be obtained through the above S5 to S7.

Example 7

A hardener crude product having a total weight of 10,000 kilograms is added into an isomerization tank, and the hardener crude product includes 7,000 kilograms of 3-methyltetrahydrophthalic anhydride (the content ratio of trans-3-methyltetrahydrophthalic anhydride to cis-3-methyltetrahydrophthalic anhydride is 1:5.6) and 3,000 kilograms of 4-methyltetrahydrophthalic anhydride.

After adding 60 kilograms of triethanolamine (alkaline catalyst), the isomerization reaction is performed at a temperature of 140° C. for 24 hours to obtain an isomerization product. After detection by gas chromatography, the content ratio of trans-3-methyltetrahydrophthalic anhydride to cis-3-methyltetrahydrophthalic anhydride in the isomerization product is 3.75:1, and the viscosity of the isomerization product is 36 cps. After that, a final isomerization product can be obtained through the above S5 to S7.

TABLE 2

|  | Example 4 | Example 5 | Example 6 | Example 7 |
|---|---|---|---|---|
| Weight ratio of 3-methyltetrahydrophthalic | 7:3 | 7:3 | 7:3 | 7:3 |

TABLE 2-continued

| | Example 4 | Example 5 | Example 6 | Example 7 |
|---|---|---|---|---|
| anhydride to 4-methyltetrahydrophthalic anhydride in the hardener crude product | | | | |
| Content ratio of trans-3-methyltetrahydrophthalic anhydride to cis-3-methyltetrahydrophthalic anhydride in the hardener crude product | 1:5.6 | 1:5.6 | 1:5.6 | 1:5.6 |
| Alkaline catalyst | Sodium hydroxide | Diethanolamine | Sodium hydroxide | Triethanolamine |
| Isomerization reaction temperature | 140° C. | 140° C. | 150° C. | 140° C. |
| Isomerization reaction time | 24 hours | 24 hours | 24 hours | 24 hours |
| Content ratio of trans-3-methyltetrahydrophthalic anhydride to cis-3-methyltetrahydrophthalic anhydride in the isomerization product | 4.03:1 | 3.64:1 | 4.31:1 | 3.75:1 |
| Isomerization product viscosity | 34 cps | 37 cps | 33 cps | 36 cps |

It can be observed from the content of Examples 4 to 7 that cis-3-methyltetrahydrophthalic anhydride can be partially reconstituted into trans-3-methyltetrahydrophthalic anhydride through use of an alkaline catalyst, thereby reducing the viscosity of the isomerization product. Specifically, the viscosity of the isomerization product is 32 cps to 38 cps. Further, it can be found from a comparison of catalytic effects of the alkaline catalysts that an inorganic base has a better reaction effect than an organic base.

Beneficial Effects of the Embodiments

In conclusion, in the method for manufacturing the methyltetrahydrophthalic anhydride provided by the present disclosure, by virtue of "adding piperylene into the reactor, so that the piperylene and the maleic anhydride undergo a first addition reaction" and "adding isoprene into the reactor, so that the isoprene and the maleic anhydride undergo a second addition reaction," the reactants can have an improved reaction efficiency. In this way, the reaction can be performed at a low temperature.

Further, in the method for manufacturing the methyltetrahydrophthalic anhydride provided by the present disclosure, since the reactants have an improved reaction efficiency, the reaction can be performed at a temperature of from 80° C. to 120° C., such that production costs are reduced. After the methyltetrahydrophthalic anhydride product is generated, an alkaline catalyst can be added for an isomerization reaction with the methyltetrahydrophthalic anhydride product, so that cis-3-methyltetrahydrophthalic anhydride is partially reconstituted into trans-3-methyltetrahydrophthalic anhydride phthalic anhydride for reducing the viscosity of the isomerization product. Accordingly, the product can have wider applicability.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for manufacturing methyltetrahydrophthalic anhydride, comprising:
adding maleic anhydride into a reactor; wherein the maleic anhydride is a limiting reagent;
introducing piperylene into the reactor in a form of gas, so as to react with the maleic anhydride for a first addition reaction at a temperature at 70° C. to form 3-methyltetrahydrophthalic anhydride; wherein a purity of the piperylene before introducing into the reactor ranges from 65% to 75%, and a duration of the first addition reaction is 12 hours when a conversion rate of the maleic anhydride reaches 70% ascertained by a gas chromatograph, the first addition reaction is completed by not introducing the piperylene; and introducing isoprene into the reactor in a form of gas, so as to react with the maleic anhydride for a second addition reaction at a temperature from 80° C. to 120° C. to form 4-methyltetrahydrophthalic anhydride and obtain a methyltetrahydrophthalic anhydride product; wherein a purity of the isoprene before introducing into the reactor is more than 99%, and a duration of the second addition reaction is 4 hours;

wherein a weight ratio of the 3-methyltetrahydrophthalic anhydride to the 4-methyltetrahydrophthalic anhydride in the methyltetrahydrophthalic anhydride product is 7:3, and a content ratio of trans-3-methyltetrahydrophthalic anhydride to cis-3-methyltetrahydrophthalic anhydride in the methyltetrahydrophthalic anhydride product is 1:5.6.

2. The method according to claim 1, wherein a content ratio of trans-3-methyltetrahydrophthalic anhydride to cis-3-methyltetrahydrophthalic anhydride in the methyltetrahydrophthalic anhydride product ranges from 1:4 to 1:7.

3. The method according to claim 1, wherein, when a content of the maleic anhydride is less than 100 ppm, the second addition reaction is completed.

4. The method according to claim 1, further comprising: adding an alkaline catalyst into the methyltetrahydrophthalic anhydride product for an isomerization reaction to convert cis-3-methyltetrahydrophthalic anhydride into trans-3-methyltetrahydrophthalic anhydride, so as to obtain an isomerization product.

5. The method according to claim 4, wherein the alkaline catalyst is selected from the group consisting of potassium carbonate, sodium carbonate, sodium hydroxide, potassium hydroxide, ethanolamine, diethanolamine and triethanolamine.

6. The method according to claim 4, wherein the isomerization reaction is performed at a temperature of from 130° C. to 160° C.

7. The method according to claim 4, wherein a content ratio of trans-3-methyltetrahydrophthalic anhydride to cis-3-methyltetrahydrophthalic anhydride in the isomerization product ranges from 1.1:1 to 4.8:1.

8. The method according to claim 7, wherein a viscosity of the isomerization product ranges from 30 cps to 50 cps.

9. A method for manufacturing methyltetrahydrophthalic anhydride, comprising:

adding maleic anhydride into a reactor; wherein the maleic anhydride is a limiting reagent;

introducing piperylene into the reactor in a form of gas, so as to react with the maleic anhydride for a first addition reaction at a temperature at 100° C. to form 3-methyltetrahydrophthalic anhydride; wherein a purity of the piperylene before introducing into the reactor ranges from 65% to 75%, and a duration of the first addition reaction is 8.5 hours when a conversion rate of the maleic anhydride reaches 50% ascertained by a gas chromatograph, the first addition reaction is completed by not introducing the piperylene; and introducing isoprene into the reactor in a form of gas, so as to react with the maleic anhydride for a second addition reaction at a temperature from 80° C. to 120° C. to form 4-methyltetrahydrophthalic anhydride and obtain a methyltetrahydrophthalic anhydride product; wherein a purity of the isoprene before introducing into the reactor is more than 99%, and a duration of the second addition reaction is 6 hours;

wherein a weight ratio of the 3-methyltetrahydrophthalic anhydride to the 4-methyltetrahydrophthalic anhydride in the methyltetrahydrophthalic anhydride product is 1:1, and a content ratio of trans-3-methyltetrahydrophthalic anhydride to cis-3-methyltetrahydrophthalic anhydride in the methyltetrahydrophthalic anhydride product is 1:5.2.

10. A method for manufacturing methyltetrahydrophthalic anhydride, comprising:

adding maleic anhydride into a reactor; wherein the maleic anhydride is a limiting reagent;

introducing piperylene into the reactor in a form of gas, so as to react with the maleic anhydride for a first addition reaction at a temperature at 100° C. to form 3-methyltetrahydrophthalic anhydride; wherein a purity of the piperylene before introducing into the reactor ranges from 65% to 75%, and a duration of the first addition reaction is 4 hours when a conversion rate of the maleic anhydride reaches 30% ascertained by a gas chromatograph, the first addition reaction is completed by not introducing the piperylene; and introducing isoprene into the reactor in a form of gas, so as to react with the maleic anhydride for a second addition reaction at a temperature from 80° C. to 120° C. to form 4-methyltetrahydrophthalic anhydride and obtain a methyltetrahydrophthalic anhydride product; wherein a purity of the isoprene before introducing into the reactor is more than 99%, and a duration of the second addition reaction is 8 hours;

wherein a weight ratio of the 3-methyltetrahydrophthalic anhydride to the 4-methyltetrahydrophthalic anhydride in the methyltetrahydrophthalic anhydride product is 3:7, and a content ratio of trans-3-methyltetrahydrophthalic anhydride to cis-3-methyltetrahydrophthalic anhydride in the methyltetrahydrophthalic anhydride product is 1:5.5.

\* \* \* \* \*